(12) United States Patent
Boulanger et al.

(10) Patent No.: US 9,404,106 B2
(45) Date of Patent: Aug. 2, 2016

(54) METHOD FOR PREVENTING, REDUCING AND/OR ELIMINATING THE FOULING OF A COMPOSITE MATERIAL

(71) Applicant: COMMISSARIAT A L'ENERGIE ATOMIQUE ET AUX ENERGIES ALTERNATIVES, Paris (FR)

(72) Inventors: Pascal Boulanger, Eguilles (FR); Alexandre Brouzes, Gif sur Yvette (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 14/349,953

(22) PCT Filed: Oct. 8, 2012

(86) PCT No.: PCT/EP2012/069851
§ 371 (c)(1),
(2) Date: Apr. 4, 2014

(87) PCT Pub. No.: WO2013/050595
PCT Pub. Date: Apr. 11, 2013

(65) Prior Publication Data
US 2014/0302579 A1 Oct. 9, 2014

(30) Foreign Application Priority Data

Oct. 7, 2011 (FR) ..................................... 11 59062

(51) Int. Cl.
| | |
|---|---|
| *B01D 65/02* | (2006.01) |
| *C12N 13/00* | (2006.01) |
| *B01D 65/08* | (2006.01) |
| *B01D 69/14* | (2006.01) |
| *B08B 17/02* | (2006.01) |
| *A61N 1/32* | (2006.01) |
| *A61B 18/00* | (2006.01) |
| *A61N 1/04* | (2006.01) |
| *B82Y 30/00* | (2011.01) |

(52) U.S. Cl.
CPC ............... *C12N 13/00* (2013.01); *B01D 65/02* (2013.01); *B01D 65/08* (2013.01); *B01D 69/141* (2013.01); *B08B 17/02* (2013.01); *A61B 2018/00613* (2013.01); *A61N 1/0412* (2013.01); *A61N 1/327* (2013.01); *B01D 2321/22* (2013.01); *B01D 2325/26* (2013.01); *B82Y 30/00* (2013.01); *Y10T 428/249921* (2015.04)

(58) Field of Classification Search
CPC ...................................................... B82Y 40/00
See application file for complete search history.

(56) References Cited

U.S. PATENT DOCUMENTS

| | | | |
|---|---|---|---|
| 5,438,025 A | 8/1995 | Leung et al. | |
| 5,707,471 A | 1/1998 | Petrak et al. | |
| 7,229,556 B1 * | 6/2007 | Hinds et al. | ............... 210/652 |
| 7,250,147 B2 | 7/2007 | Tour et al. | |
| 7,611,628 B1 | 11/2009 | Hinds, III | |
| 8,519,530 B2 * | 8/2013 | Tse et al. | ................. 257/706 |
| 2004/0071624 A1 | 4/2004 | Tour et al. | |
| 2004/0173506 A1 | 9/2004 | Doktycz et al. | |
| 2006/0171874 A1 | 8/2006 | Khabashesku et al. | |
| 2008/0041791 A1 * | 2/2008 | Cooper et al. | ................. 210/695 |
| 2008/0145706 A1 | 6/2008 | Mevellec et al. | |
| 2008/0152949 A1 | 6/2008 | Mevellec et al. | |
| 2008/0193668 A1 | 8/2008 | Mevellec et al. | |
| 2008/0223795 A1 | 9/2008 | Bakajin et al. | |
| 2009/0117391 A1 | 5/2009 | Mevellec et al. | |
| 2009/0298994 A1 | 12/2009 | Dubois et al. | |
| 2010/0003402 A1 | 1/2010 | Stout et al. | |
| 2011/0108424 A1 | 5/2011 | Puget et al. | |
| 2011/0207378 A1 | 8/2011 | Defoort et al. | |
| 2011/0244585 A1 | 10/2011 | Mayne-L'Hermite et al. | |
| 2012/0071587 A1 | 3/2012 | Defoort et al. | |
| 2012/0196035 A1 | 8/2012 | Deniau et al. | |
| 2012/0224944 A1 | 9/2012 | Boulanger et al. | |
| 2012/0228839 A1 | 9/2012 | Boulanger et al. | |
| 2013/0108865 A1 | 5/2013 | Boulanger et al. | |
| 2013/0189586 A1 | 7/2013 | Sarrazin et al. | |
| 2013/0256280 A1 | 10/2013 | Boulanger et al. | |

FOREIGN PATENT DOCUMENTS

| | | |
|---|---|---|
| WO | 02060812 A2 | 8/2002 |
| WO | 03049219 A1 | 6/2003 |
| WO | 2004080578 A1 | 9/2004 |
| WO | 2007025104 A2 | 3/2007 |
| WO | 2008028155 A2 | 3/2008 |
| WO | 2008062378 A2 | 5/2008 |
| WO | 2008078052 A2 | 7/2008 |
| WO | 2009141528 A2 | 11/2009 |
| WO | 2009148959 A2 | 12/2009 |
| WO | 2010002805 A1 | 1/2010 |
| WO | 2011063458 A1 | 6/2011 |

OTHER PUBLICATIONS

Bahr, J., et al., "Covalent chemistry of single-wall carbon nanotubes", "J. Mater. Chem.", May 1, 2002, pp. 1952-1958, vol. 12.
Bonard, J., et al., "Field Emission of Individual Carbon Nanotubes in the Scanning Electron Microscope", "Physical Review Letters", Nov. 2, 2002, pp. 197602-1 to 197602-4, vol. 89, No. 19.

(Continued)

*Primary Examiner* — Ralph Gitomer
(74) *Attorney, Agent, or Firm* — Hultquist, PLLC; Mary B. Grant (57) ABSTRACT

A method for preventing, reducing and/or eliminating the fouling of a composite material is provided, the composite material comprising (1) a plurality of conductive or semiconductive nanotubes, which are aligned parallel to one another, and (2) a matrix arranged between the conductive or semiconductive nanotubes, the composite material in the form of an isoporous membrane with nanopores which correspond to the pores of the conductive or semiconductive nanotubes and optionally to the pores of the matrix arranged between the conductive or semiconductive nanotubes, the method comprising applying an electric field to the composite material, wherein the fouling is prevented, reduced and/or eliminated at the surface, at and in the pores of the composite material.

5 Claims, 3 Drawing Sheets

(56) References Cited

OTHER PUBLICATIONS

Brady-Estevez, A., et al., "Multiwalled Carbon Nanotube Filter: Improving Viral Removal at Low Pressure", "Langmuir", Aug. 26, 2010, pp. 14975-14982, vol. 26, No. 18.

Cui, Z., et al., "The use of gas bubbling to enhance membrane processes", "Journal of Membrane Science", Aug. 2, 2003, pp. 1-35, vol. 221, No. 1-2.

Fan, D., et al., "Synthesis of polymer grafted carbon nanotubes by nitroxide mediated radical polymerization in the presence of spin-labeled carbon nanotubes", "European Polymer Journal", Nov. 13, 2006, pp. 26-34, vol. 43.

Garcia, E., et al., "Fabrication and multifunctional properties of a hybrid laminate with aligned carbon nanotubes grown In Situ", "Composites Science and Technology", Mar. 7, 2008, pp. 2034-2041, vol. 68.

Hinds, B., et al., "Aligned Multiwalled Carbon Nanotube Membranes", "Science", Jan. 2, 2004, pp. 62-65, vol. 303.

Holt, J., et al., "Fast Mass Transport Through Sub-2-Nanometer Carbon Nanotubes", "Science", May 19, 2006, pp. 1034-1037, vol. 312.

Hu, H., et al., "Sidewall Functionalization of Single-Walled Carbon Nanotubes by Addition of Dichlorocarbene", "J. Am. Chem. Soc.", Nov. 11, 2003, pp. 14893-14900, vol. 125.

Hummer, G., et al., "Water conduction through the hydrophobic channel of a carbon nanotube", "Nature", Nov. 8, 2001, pp. 188-190, vol. 414.

Kang, S., et al., "Single-walled carbon nanotubes exhibit strong antimicrobial activity", "Langmuir", Jul. 21, 2007, pp. 8670-8673, vol. 23, No. 17.

Khare, R., et al., "Carbon Nanotube Based Composites—A Review", "Journal of Minerals and Materials Characterization and Engineering", Jun. 2005, pp. 31-46, vol. 4, No. 1.

Kim, S., et al., "Scalable Fabrication of Carbon Nanotube/Polymer Nanocomposite Membranes for High Flux Gas Transport", "Nano Letters", Aug. 9, 2007, pp. 2806-2811, vol. 7, No. 9.

Lyskawa, J., et al., "Direct Modification of a Gold Electrode with Aminophenyl Groups by Electrochemical Reduction of in Situ Generated Aminophenyl Monodiazonium Cations", "Chem. Mater.", Sep. 9, 2006, pp. 4755-4763, vol. 18.

Marchand, M., "Synthese In-Situ et Caracterisation de Nanotubes de Carbone Individuels Sous Emission de Champ", Nov. 16, 2009, pp. 62-69, Thesis. Physics. Universit Claude Bernard—Lyon I, 2009. French.

Marchand, M., "Synthese In-Situ et Caracterisation de Nanotubes de Carbone Individuels Sous Emission de Champ", Nov. 16, 2009, pp. 62-69 (Machine Translation), Thesis. Physics. Universit Claude Bernard—Lyon I, 2009. French.

Marcoux, P., et al., "Electrochemical functionalization of nanotube films: growth of aryl chains on single-walled nanotubes", "New J. Chem.", Jan. 16, 2004, pp. 302-307, vol. 28.

Menzel, R., et al., "Inverse Gas Chromatography of As-Received and Modified Carbon Nanotubes", "Langmuir", Jun. 3, 2009, pp. 8340-8348, vol. 25, No. 14.

Mevellec, V., et al., "Grafting Polymers on Surfaces: A New Powerful and Versatile Diazonium Salt-Based One-Step Process in Aqueous Media", "Chem. Mater.", Nov. 8, 2007, pp. 6323-6330, vol. 19.

Mi, W., et al., "Vertically aligned carbon nanotube membranes on macroporous alumina supports", "Journal of Membrane Science", Jul. 21, 2007, pp. 1-7, vol. 304.

Mierczynska, A., et al., "Electrical and Mechanical Properties of Carbon Nanotube/Ultrahigh-Molecular-Weight Polyethylene Composites Prepared by a Filler Prelocalization Method", "Journal of Applied Polymer Science", Apr. 10, 2007, pp. 158-168, vol. 105.

Naficy, S., et al., "Modulated release of dexamethasone from chitosan-carbon nanotube films", "Sensors and Actuators A: Physical", Aug. 3, 2009, pp. 120-124, vol. 155.

Nan, C., et al., "A simple model for thermal conductivity of carbon nanotube-based composites", "Chemical Physics Letters", Jul. 10, 2003, pp. 666-669, vol. 375.

Oh, S., et al., "Preparation of Aligned Carbon Nanotube Films Using the Langmuir-Blodgett Technique", "Int. Conf. Nanotech.", May 7, 2006, Page(s) (Abstract Only).

Park, H., et al., "A High-Flux, Flexible Membrane with Parylene-encapsulated Carbon Nanotubes", "Nanotech 2008 Conference", Mar. 20, 2008, Publisher: Lawrence Livermore National Laboratory, Published in: Boston, MA.

Peinemann, K., et al. (EDS), Front Matter, in Membrane Technology: Membranes for Water Treatment, vol. 4, Mar. 2010, pp. i-xiv, Publisher: Wiley-VCH Verlag GmBH & Co. KGaA, Published in: Weinheim, Germany. doi: 10.1002/9783527631407.fmatte.

Pichot, V., et al., "Evidence of strong nanotube alignment and for iron preferential growth axis in multiwalled carbon nanotube carpets", "Appl. Phys. Lett.", Jul. 19, 2004, pp. 473-475, vol. 85, No. 3.

Pichot, V., et al., "Structural and mechanical properties of single-wall carbon nanotube fibers", "Physical Review B", Dec. 13, 2006, pp. 245416-1-245416-8, vol. 74.

Pinault, M., et al., "Evidence of Sequential Lift in Growth of Aligned Multiwalled Carbon Nanotube Multilayers", "Nano Letters", Nov. 8, 2005, pp. 2394-2398, vol. 5, No. 12.

Poh, Z., et al., "Fabrication and electrochemical behavior of vertically-aligned carbon nanotube electrodes covalently attached to p-type silicon via a thioester linkage", "Materials Letters", Jan. 6, 2009, pp. 757-760, vol. 63.

Rojas-Chapana, J., et al., "Multi-walled carbon nanotubes for plasmid delivery into *Escherichia coli* cells", "Lab on a Chip", Mar. 10, 2005, pp. 536-539, vol. 5.

Tessier, L., et al., "Grafting organic polymer films on surfaces of carbon nanotubes by surface electroinitiated emulsion polymerization", "Phys. Stat. Sol. (a)", May 15, 2008, pp. 1412-1418, vol. 6.

Tian, S., et al., "Fabrication and performances of epoxy/multi-walled carbon nanotubes/piezoelectric ceramic composites as rigid piezo-damping materials", "J. Mater. Sci.", Jun. 3, 2008, pp. 4979-4987, vol. 43.

Wang, Y., et al., "Microwave-induced rapid chemical functionalization of single-walled carbon nanotubes", "Carbon", Jan. 21, 2005, pp. 1015-1020, vol. 43.

Yantzi, J., et al., "Carbon nanotube enhanced pulsed electric field electroporation for biomedical applications", Mechatronics and Automation, 2005 IEEE International Conference, Jul. 29, 2005, pp. 1872-1877, vol. 4, Publisher: IEEE.

* cited by examiner

METHOD FOR PREVENTING, REDUCING AND/OR ELIMINATING THE FOULING OF A COMPOSITE MATERIAL

CROSS-REFERENCE TO RELATED APPLICATIONS

This application is a U.S. national phase under the provisions of 35 U.S.C. §371 of International Patent Application No. PCT/EP12/69851 filed Oct. 8, 2012, which in turn claims priority of French Patent Application No. 1159062 filed Oct. 7, 2011. The disclosures of such international patent application and French priority patent application are hereby incorporated herein by reference in their respective entireties, for all purposes.

TECHNICAL FIELD

The present invention concerns the field of nanotechnologies and more particularly the field of materials containing nano-objects such as conductive or semiconductive nanotubes and devices containing these materials.

Therefore the present invention concerns a device comprising (1) at least one material composed of an assembly of conductive or semiconductive nanotubes that in particular are aligned, coated or covered by a matrix and (2) means allowing the polarisation of this material i.e. to subject this material to an electric field.

The present invention not only relates to said device but also to the different uses thereof in particular for cleaning or modifying membranes such as filtration membranes, and for the electroporation of substrates such as cells.

STATE OF THE PRIOR ART

Membrane filtering through porous or dense membranes has been known since the first experiments by Abbé Nolet, and has been used industrially in particular since the work done by Sourirajan. Different types of filtration are currently used in relation to pore size. Therefore, a distinction is made between:
  microfiltration with porous membranes whose pores are in the order of one micrometer, used to retain bacteria;
  ultrafiltration with porous membranes formed of mesopores, used to retain macromolecules and viruses;
  nanofiltration with porous membranes formed of micropores, used to treat drinking water (retention of micro-pollutants);
  reverse osmosis with dense membranes used to desalinate seawater.

In parallel, nano-objects are currently the focus of particular interest on account of their original properties heightened in comparison with conventional materials. Indeed, nano-objects have numerous advantages both regarding their structures and physical properties but also regarding their potential applications in particular in membranes or in any other physical separation device, composite materials, coatings, thermal, optical or electronic devices, electrodes, and catalyst carriers and devices for storing or converting chemical, light, electrical, mechanical energy, etc.

Among nano-objects, carbon nanotubes (CNTs) discovered in 1991 are the subject of numerous research studies and applications. For example, one particular use of CNTs is to impregnate them in a matrix allowing a composite multifunctional material to be obtained, such as a membrane particularly useful for filtration, a coating having active properties or a multifunctional electrode.

Indeed, in the field of membrane applications, it has been predicted by simulation and shown experimentally that under certain conditions, the flow velocity of water in the core of CNTs could be up to 1000 times faster than the velocity predicted by conventional diffusion laws [1]. The term <<facilitated transport>> is used which is defined as the transport of water molecules in a spatial organisation which limits friction of the molecules between each other and with the walls of a pore and leads to flow velocities higher than conventional transport laws. This is also the case, but to a lesser extent, for neutral or ionic liquids and gases. The forming of membranes based on aligned nanotubes has been shown experimentally using several methods.

Whether or not membranes contain CNTs and irrespective of their application, they are subject to clogging. The pores of membranes become clogged under the combined effect of (1) ageing of the material, (2) accumulation in the pores of compounds of the solutions to be filtered and (3) the onset in the pores or on the surface of the membrane of an organic film which develops and clogs the pores. This phenomenon is known under the name <<bio-fouling>>, and is the consequence of the accumulation, growth and proliferation of a <<biofilm>> formed of residues of biological species and microorganisms such as bacteria.

To prevent the fouling of membranes, numerous prevention and treatment strategies have been used but they are essentially based on:
  prevention via surface treatment with bactericidal layers of different types (chemical or nanoparticles). It is to be noted that membranes having nanoparticles and/or CNTs are intrinsically more resistant to biofilm proliferation on account of their electrical properties ([2] and [3]) and the hydrophobic fakir-mat structure of CNTs.
  the use of chemical compounds which will chemically destroy germs, crystals and delay the onset of clogging: i.e. cleaning, washing. This treatment is a chemical treatment essentially based on chlorine or anti-fouling products which themselves will have a tendency over the longer term of becoming deposited on the membranes. These precipitations must be prevented with other chemical treatments. This type of treatment is the only one which can be used for asymmetric membranes, and in particular for seawater desalination membranes.
  the use of a back-wash technique whereby the membrane is caused to operate by reversing its standard flow to <<unstick>> the particles/organisms which have lodged themselves inside the pores. This strategy is used in particular for so-called <<symmetric>> membranes which allow the passing of solutes in both directions.

Mention can also be made of techniques having recourse to active strategies such as placing the membrane in vibration for example using piezoelectric techniques [4] or by oxidizing the clogging products [5], or by generating gas bubbles directly at the interface acting as <<slug flow>> known for its efficacy in other systems [6].

Another technique currently under development is to understand how to make use of this foulant or biofilm so that it self-regulates without damaging the membrane. This strategy is especially applied to the case of fouling by organic products and is based on precise knowledge of the biofilm development mode for limiting thereof.

CNTs, when subjected to voltages, can enhance the so-called field emission phenomenon via tip enhancement effect, the result of which is to increase the emitted field at a given voltage in relation to a non-structured material. Individual CNTs have been massively used for field emission studies [7]. Their cylindrical geometric shape (form factor>100), coupled with their electronic conduction properties (ballistic transport over 100 nm$^{-1}$, transportable current density>10$^9$ A/cm$^2$, close electron and hole mobility<10$^5$ cm$^2$/V·s) and high chemical, thermal and mechanical stability all contribute to making them an ideal material for field emission.

Similarly, numerous studies relate to the placing under high voltage of essentially individualised CNTs. These, in addition to the field effect (tip or wall), mention particular behaviours. Indeed, if the voltage applied to the nanotube is too strong, it can either destroy itself from one of its ends, or break in the vicinity of its centre. In addition, the applying of a voltage to nanotubes is already known to have a beneficial effect both for their synthesis (Plasma Enhanced Chemical Vapour Deposition—PECVD) and the quality of their crystallinity.

The theoretical formulas are not simple and explicit, but with a membrane of density 10$^9$ nanotubes/cm$^2$ having nanotubes of inner diameter 1 nm and length of 100 nm, the improvement in intensity of the field effect compared with a conventional metal electrode can be estimated at a factor (i.e. intensity of the magnetic field emitted by the surface for an equivalent applied voltage)>500 for a single nanotube [8]. For a mat whose nanotubes are spaced apart by 100 nm, it is reduced by a factor of 10 (i.e. >50 in total).

Advantage is taken of this phenomenon essentially to form screens (field emission for electron emission). The behaviour of individualised nanotubes under a field is also taken advantage of in order to align them (dielectrophoresis). Individually they also act to have a local amplification effect.

The use of the field effect emitted by carbon nanotubes has also been proposed for the electroporation of cells.

It is recalled that cell electroporation is a technique which has been known for several decades. It is a technique whereby a variable electric field is applied to a solution containing biological cells, proteins, even organs (the case with electrotransfer for vectoring medicinal substances or DNA). In relation to the applied voltage, the action of the pulsed field will cause reversible or irreversible actions on the constituents of biological origin subjected thereto such as (i) opening of pores i.e. creation of pores or permeabilization of the plasma membrane; (ii) bursting of the plasma membrane; (iii) denaturing of proteins and biopolymers.

Conventional electroporation requires the use of intense pulsed fields in the order of 10$^4$ to 10$^5$ V/cm necessitating specific electrodes and high power voltages.

The choice of the different functions of use is based on the choice of power voltage (pulse intensity) and power cycle (number of pulses and space between pulses). The higher the voltage and the more cycle length is increased, the stronger the irreversible effect. With a low voltage, cells can be electroporated without being destroyed, and with a high voltage the cells burst and are eliminated. Similarly, the more the pulses are numerous and closer together, the stronger the effect. It is easy in the state of the art to find protocols and electric field intensity values with which it is possible to obtain cell inactivation or permeabilization respectively by electroporation, both for microorganisms and for animal cells.

Yantzi and Yeow have shown that it is possible to make use of mats of alone, randomly aligned nanotubes as electrode for electroporation systems [9]. Similarly, the use of nanotubes as vectors for cell electroporation has already been proposed for nanotubes in solution whereby the contacting of the cell is obtained on the walls of the tubes and not on the tip [10].

In different manner, Rojas-Chapana et al [11] and the inventors of international application WO 2008/062378 [10] have shown that the field effect emitted by nanotubes dispersed in solution can be used to enhance inter-electrode voltage. Since some cells have the property of adhering to the nanotubes, they are directly subjected to a local field (re-emission by the tip of the nanotubes in solution) that is stronger than the surrounding field. In reference [11] use is made of the axial field effect, which corresponds to the field along the axis of the tube and which is the strongest, whereas in reference [12] the radial field effect is used, the latter is perpendicular to the axis of the tubes, at the point where the cells adhere.

The inventors have set themselves the objective of proposing a membrane better resistant to fouling than prior art membranes but which also allows easier de-fouling strategies, and an electrode which can be used for cell electroporation.

DESCRIPTION OF THE INVENTION

The present invention allows the solving of the technical problems such as previously defined, and the achieving of the objective that the inventors have set themselves.

The work conducted by the inventors has taken advantage of the properties of the field effect emitted by nanotubes included in a composite material of the type of nanotubes impregnated with or incorporated in a matrix, and subjected to an electrical field, and in particular materials having a mat of aligned nanotubes advantageously of high density. Therefore, the aligned nanotubes may have a density, expressed in nanotubes/cm$^2$, equal to or higher than 10$^5$ and in particular equal to or higher than 10$^9$. With said use it is possible to limit, reduce and/or prevent the fouling of membranes comprising such materials.

Therefore the present invention proposes an <<electrical>> alternative to the cleaning of nanotube-based membranes, in particular mats of aligned nanotubes using the principle of electroporation for the continuous destruction in operation of a biofilm in the early stages of the formation thereof and/or once it has formed.

In remarkable manner, this field effect can also be used for the electroporation of substrates. The producing of electroporation devices for biological applications can benefit from the advantages of aligned nanotubes since these have field emission properties which allow a reduction in the applied voltages and a reduction in the size of the device thereby making the device more compact and more solid thanks to the impregnating of the nanotubes; and this technique is compatible with integrated systems of <<biochip>> or <<lab-on-chip>> type. The impregnated mat of aligned nanotubes is then used as electroporation electrode.

Of interest is the fact that the present invention applies not only to CNTs but also to any type of semiconductive or conductive nanotubes.

More particularly the present invention concerns a device comprising:

i) a composite material comprising (1) a plurality of conductive or semiconductive nanotubes, and (2) a matrix arranged between these nanotubes; and ii) means allowing said composite material to be subjected to an electric field.

In the present invention, by <<nanotube>> is meant a tubular and/or cylindrical structure whose inner diameter varies between 0.5 nm and 100 nm, in particular between 0.5 nm and 50 nm and more specifically for nanofiltration applications between 0.5 nm and 10 nm. The outer diameter of such structures varies between 0.5 nm and 100 nm, in particular between 0.5 nm and 50 nm and more specifically for nanofiltration applications between 0.5 nm and 10 nm.

The conductive or semiconductive nanotubes used in the present invention may be inorganic nanotubes, organic nanotubes or a mixture of inorganic nanotubes and organic nanotubes.

Therefore, all or part of the conductive or semiconductive nanotubes used can be inorganic nanotubes. Said inorganic nanotubes are advantageously chosen from the group consisting of zinc oxide nanotubes (ZnO), gallium nitride nanotubes (GaN), boron nitride nanotubes (BN), tungsten bisulfide nanotubes ($WS_2$), molybdenum bisulfide nanotubes ($MoS_2$), tungsten diselenide nanotubes ($WSe_2$), titanium dioxide nanotubes ($TiO_2$) or molybdenum trioxide nanotubes ($MoO_3$), or one of the mixtures thereof.

Among the nanotubes which can be used in the present invention, it is to be noted that some such as boron nitride nanotubes (BN) have intrinsic piezoelectric properties.

Similarly, all or part of the conductive or semiconductive nanotubes used may be organic nanotubes. Said organic nanotubes are advantageously carbon nanotubes. A carbon nanotube is defined as a concentric winding of one (or more) layers of graphene (hexagonal mesh of carbon). The following terms are used:
  Single Wall NanoTubes or SWNTs if there is a single layer of graphene;
  Double Wall NanoTubes or DWNTs if there are two layers of graphene;
  Multi-Wall NanoTubes or MWNTs if there are several layers of graphene.

The present invention applies to any type of carbon nanotube irrespective of the preparation method. For example, the carbon nanotubes used in the present invention may be nanotubes with a single layer of graphene (SWNT), nanotubes with two layers of graphene (DWNT), nanotubes with several layers of graphene (MWNT) or one of their mixtures.

Those skilled in the art know different methods to prepare nanotubes such as previously defined. As more particular examples of methods allowing the preparation of CNTs, mention can be made of physical methods based on the sublimation of carbon such as electric arc, laser ablation methods or those using a solar oven, and chemical methods such as the CVD method or the pyrolysis of carbon sources on metal catalysts.

Mats of aligned CNTs are advantageously obtained by simultaneous and parallel growth of single nanotubes, perpendicular to a substrate to which they are attached. The technique most particularly used for the growth of such ordered structures is CVD and in particular CVD with the pre-depositing of a catalyst or with simultaneous co-injection of a catalyst and carbon sources.

The nanotubes used in the present invention can have any chirality and any length. Advantageously, these nanotubes have a length of between 10 nm and 2 cm, in particular between 20 nm and 1 mm, more particularly between 50 nm and 100 μm, most particularly between 100 nm and 50 μm.

In the composite material used in the present invention, the nanotubes relative to one another may have an aligned, offset or dispersed conformation. By <<offset conformation>> is meant substantially straight nanotubes but not necessarily aligned relative to one another.

However, an aligned conformation is preferred in the present invention. With such an aligned conformation, the nanotubes are used aligned relative to one another in a vertical array. In this conformation, they are generally and substantially perpendicular to a support. In other words, the nanotubes are aligned parallel to one another and advantageously vertically in a vertical array. The terms <<mat>>, <<forest>> or <<lattice>> of nanotubes are used.

An aligned conformation can be obtained when preparing the nanotubes or once they have been prepared, in particular using filtration techniques in the core of the nanotubes such as described in international application WO 2008/028155 [12] or techniques using a flow transverse to the axis of the tubes such as described in patent application US 2004/0173506 [13] and international application WO 2009/141528 [14].

The density of nanotubes in the material according to the present invention may be variable. It is advantageously between $10^4$ and $10^{13}$ nanotubes/$cm^2$ of material. The notion of nanotube density is well known to those skilled in the art and corresponds to the number of nanotubes aligned per surface unit. This density is conventionally measured by counting electronic microscope images of the nanotubes (absolute count).

Density, alignment and tortuosity of nanotubes are also parameters which can be accessed by X-ray measurements, in particular as described in the article by Pichot et al, 2004 [15] for MWNTs.

In the composite material used in the present invention, the matrix arranged between the nanotubes i.e. the filling matrix can be chosen from the group consisting of a ceramic matrix, polymer matrix, metal matrix, a matrix derived from biomass or a matrix derived from cellulose derivatives, and mixtures thereof.

By <<ceramic matrix>> is more particularly meant a matrix whose constituent material is chosen from the group consisting of a sol-gel material, silicon nitride, aluminium nitride, titanium nitride, aluminium carbide, titanium carbide, silicon carbide, silicon oxide, silicon dioxide, magnesium oxide, cerium oxide, alumina, titanium oxide, bismuth oxide, beryllium oxide, hydroxyapatite, or a mixture thereof.

The polymer matrix used in the present invention may be formed of one or more thermoplastic polymer(s), one or more thermosetting polymer(s), one or more glassy polymer(s) or a mixture thereof. By <<polymer matrix>> is more particularly meant a matrix whose constituent material is chosen from the group consisting of a polyamide, polyimide, parylene, polycarbonate, polydimethylsiloxane, polyolefin, polysulfone, polyethersulfone, polyetheretherketone (PEEK) and its derivatives, a polypropylene (PP), polyvinylidene fluoride (PVDF), polyvinyl pyrrolidone (PVP), cellulose acetate (AC), acrylic resin, polystyrene (PS), polymethylmethacrylate (PMMA), polymethacrylate (PMA), epoxy resin, polyester, acetylnitrile-butadiene-styrene, or a mixture thereof.

In addition the filling matrix, in particular if it is a polymer matrix, and its constituent material can be substituted by at least one reactive function. By <<reactive function>> in the present invention is meant a function chosen from among a carboxyl function (able to react with an amine or alcohol function), an aryl group (e.g. pyrene, naphthalene or polyaromatics), a radical entity, a hydroxyl function or alcohol function (able to react with a carboxyl or isocyanate function), an amine function (able to react with an ester function), an ester function (able to react with an amine function), an aldehyde function (able to react with a hydrazide function), a hydrazide function (able to react with an aldehyde function), a ketone function (able to react with two alcohol functions for acetalysation), an epoxy function (able to react with an amine function), an isocyanate function (able to react with a hydroxyl function), a maleimide function (able to react with a thiol function, an amine function or a diene function), a diene function (able to react with a maleimide function) and a thiol function (able to react with a maleimide function or another thiol function).

The filling matrix may be non-porous or porous. A porous matrix of type polyamide, polysulfone, polyestersulfone, PP, PVDF, PVP or cellulose acetate may be of particular advantage if the composite material of the invention is used for seawater or brackish water desalinating operations.

As a variant, the composite material used in the present invention is used as filtration membrane, the filling matrix possibly being a water-impermeable structure to promote the passing of liquid to be filtered within the nanotubes.

As a further variant, if the composite material used in the present invention is used as electrode, the filling matrix is a conductive or insulating matrix and advantageously an insulating matrix.

Therefore, the composite material used in the present invention can be an electrode or membrane. It may also be a carbon nanotube-based hydrophobic coating and in particular a marine anti-fouling coating. It is recalled that a carbon nanotube-based hydrophobic coating has superfluidity properties when water for example slips over its surface.

Any technique known to those skilled in the art for arranging a matrix between nanotubes can be applied for preparing the composite material which can be used in the present invention. With this step it is possible to fill the residual inter-nanotube space with a matrix such as previously defined.

This technique may be chemical vapour phase deposit (CVD), atomic layer deposit (ALD), deposit by spin coating; impregnation whether or not pressure-assisted; photo-impregnation; etc.

Also, the filling matrix can be arranged in the entire space between the nanotubes or on the contrary in certain parts of this space, leaving other parts of the space free between the nanotubes. On the contrary, the filling matrix can be arranged so that the nanotubes are embedded in the matrix.

The composite material used in the present invention may therefore be in the form an isoporous membrane whose nanopores correspond to the pores of the nanotubes, and optionally to the pores of the filler matrix. In said material, the nanotubes are said to be <<through>> nanotubes. The nanotubes open into at least one side of the composite material, and particularly into two opposite sides of the composite material. In this configuration, the nanotubes are also said to be <<flow-through>> insofar as all or part of the nanotubes take part in the transport of species during filtration via the membrane (i.e. the composite material).

In one most particular embodiment of the composite material used in the present invention, the nanotubes are grafted covalently (or functionalized or derivatized) with at least one organic polymer, before they are incorporated by the filling matrix. In other words, at least one organic polymer is covalently grafted onto each nanotube.

The work conducted by the inventors has shown that by adding an adhesion layer bonded covalently onto nanotubes, in particular aligned nanotubes, prior to their impregnation by (or their incorporation in) a matrix, in particular a polymer matrix, makes it possible to improve the interface between nanotubes and matrix.

First, the fact that the adhesion layer is covalently grafted onto the surface the nanotubes strengthens the bond with the nanotubes and therefore allows better adherence of the filling matrix on the nanotubes. During the impregnation step, the filling matrix strongly interacts with the previously grafted layer. The interpenetrated latticework thus obtained improves the quality of the nanotubes/matrix interface and reinforces the mechanical properties of the material.

In addition, this interpenetration can be accompanied by physisorption but also by chemisorption further strengthening the interactions between the adhesion layer and the filling matrix. With chemisorption there may exist ionic bonds or covalent bonds involving an atom of the adhesion layer and an atom of the constituent material of the filling matrix.

Therefore a better interface between the sub-layer and the matrix translates as improved mechanical strength and improved imperviousness of the inter-nanotube space. For filling matrices of polymer type, the stronger interpenetration of the polymer chains of the sub-layer with the chains of the constituent material of the filling matrix promotes continuity between these chains.

The improvement in the nanotube/matrix interface also reduces the diffusion pathways of liquids and/or gases in the material and allows both better imperviousness of the inter-tube space if this is desired and also better selectivity by preventing those species it is desired to sort from remixing via these secondary diffusion pathways.

The use of an adhesion layer and adapted functionalization allows better compatibility with the material of the filling matrix, and the filling by this matrix of the inter-nanotube space can be partial or total. For example, partial filling of the inter-tube space can be used to change the hydrophobicity of the nanotubes and to control their wettability but also to create a layer of adsorption sites so as to convert the nanotubes and in particular the mats they form, to a sensor, electrode or selective filter.

By <<organic polymer>> is meant a polymer whose main chain chiefly comprises carbon atoms but may also comprise heteroatoms such as oxygen atoms and nitrogen atoms.

This organic polymer is advantageously covalently grafted onto the outer lateral part of the nanotubes. This grafting can be located on limited regions defined by these surfaces.

Each nanotube may comprise at least one, at least two, at least five, at least ten, at least 20 or at least 100 grafted organic polymers, each grafted organic polymer on one same nanotube possibly having an identical or different unit sequence from the other grafted polymer(s). Similarly, the organic polymers grafted on different nanotubes may have an identical or different unit sequence for all the nanotubes.

The organic polymer used in the present invention comprises:
  at least one unit derived from a cleavable aryl salt, and/or
  at least one unit derived from a monomer having at least one bond of ethylenic type, and/or
  at least one unit derived from a monomer having at least two carboxylic functions, and/or
  at least one unit derived from a monomer having at least two amine functions, and/or
  at least one unit derived from a monomer having a carboxylic function and an amine function. The organic polymer used in the present invention is advantageously formed of recurrent pattern units corresponding to such units.

The adhesion layer formed by the organic polymers grafted on the nanotubes may contain another nanoscopic material, such as metal nanoparticles in particular (Cu, Ar, Ag, Co, Si, Au, Ti, Pd, Cr, Al or Pt) or metal oxides ($TiO_2$, TiO, etc.).

Advantageously, the organic polymer used in the present invention is substituted by at least one reactive function such as previously defined.

By <<cleavable aryl salt>> in the present invention is meant a cleavable aryl salt chosen from the group consisting of aryl diazonium salts, aryl ammonium salts, aryl phosphonium salts, aryl iodonium salts and aryl sulfonium salts. More particularly, a cleavable aryl salt which can be used in the present invention has the following formula (I):

$$R\text{—}N_2^+, A^- \qquad (I)$$

in which:
  A is a monovalent anion, chosen in particular from among inorganic anions e.g. halides such as $I^-$, $Br^-$ and $Cl^-$, halogenoborates such as tetrafluoroborate, perchlorates and sulfonates, and organic anions such as alcoholates and carboxylates; and R represents an aryl group, corresponding to an aromatic or heteroaromatic carbon structure optionally mono- or polysubstituted, formed of one or more aromatic or heteroaromatic rings each having 3 to 8 atoms, the heteroatom(s) possibly being N, O, P or S. The substituent(s) may contain one or more heteroatoms such as N, O, F, Cl, P, Si, Br or S, and $C_1$ to $C_6$ alkyl groups or $C_4$ to $C_{12}$ thioalkyl groups in particular.

By >> monomer having at least one bond of ethylenic type>> is advantageously meant a monomer having a vinylic unsaturation, an allylic unsaturation and/or an acrylic unsaturation.

Said monomers are chosen from among the monomers of following formula (II)

(II)

in which the $R_1$ to $R_4$ groups, either identical or different, represent a non-metallic monovalent atom such as a halogen atom, a hydrogen atom, a saturated or unsaturated chemical group such as an alkyl, aryl group, a —$COOR_5$ group in which $R_5$ represents a hydrogen atom or $C_1$-$C_{12}$ alkyl group and preferably $C_1$-$C_6$, a nitrile, a carbonyl, an amine or an amide. Advantageously, the monomers having at least one ethylenic bond used in the present invention are substituted by at least one reactive function such as previously defined.

The method for preparing the particular composite material such as previously defined (i.e. grafted nanotubes+filling matrix) and used in the device of the invention comprises the following successive steps of:

a) grafting at least one organic polymer on the plurality of nanotubes, b) arranging a matrix such as previously defined between the nanotubes obtained after step (a). Step (b) of the method has already been explained.

At step (a) of the method for preparing a composite material, any technique allowing the grafting of an organic polymer can be used. This technique is advantageously chosen from among:

functionalization of the nanotubes followed by coupling with an organic polymer [16];

radical chemical grafting based on the method described in international application WO 2008/078052 [17] and in the article by Mévellec et al 2007 [18];

electrografting, further information on electrografting onto carbon nanotubes can be found in the article by Tessier et al, 2008 [19];

photografting;

grafting by Atom Transfer Radical Polymerization (ATRP);

grafting by Nitroxide Mediated Radical Polymerization (NMRP);

grafting by Reversible Addition Fragmentation chain Transfer (RAFT), or MAcromolecular Design via Interchange of Xanthane (MADIX);

vapour phase grafting; or microwave-activated grafting.

More detailed information on the other grafting techniques which can be used at step (a) of the method for preparing the composite material used in the present invention can be obtained from the article by Fan et al, 2007 [20] and in the articles cited by the latter.

It is to be pointed out that the methods used for preparing the adhesion layer do not disturb the alignment of the nanotubes. It is therefore possible to have a material having a dense mat of aligned nanotubes, in the order of $10^5$ to $10^{13}$ nanotubes/$cm^2$ and in particular in the order of $10^9$ to $10^{11}$ nanotubes/$cm^2$. Advantageously the maximum misalignment obtained, after covalent grafting of the organic polymers, for a dense mat of nanotubes is 10 degrees and the maximum tortuosity is 3%, and in particular a misalignment of 5% for a tortuosity of 1%.

As previously explained, the combined use of an adhesion layer and a filling matrix makes it possible to obtain a much more solid composite material than a mat of nanotubes alone. The nanotubes, particularly aligned nanotubes of the invention are held in place mechanically, which allows a membrane or electrode to be obtained that is much more solid than the prior art membranes and electrodes.

The composite material used in the device of the invention, with or without an adhesion layer, can be in the form of a membrane or electrode. If the composite material is used as electrode, it can be arranged on or supported by an element such as a silicon element. However the self-standing nature of the composite material, in particular when having an adhesion layer, means that such support is optional and non-compulsory unlike the case with some prior art electrodes.

For applications as membrane, the composite material used in the present invention has a filling matrix that is advantageously porous or non-porous, as previously explained.

For applications as electrode, the composite material used in the present invention has a conductive or insulating filling matrix.

In addition, irrespective of the matrix, electric conduction occurs along the axis of the nanotubes but also perpendicular to this axis. Indeed, parasitic contacts exist and they reduce the field but allow facilitated powering. It is effectively no longer necessary to contact the entire base of the electrode or of the membrane. For example, for a carbon nanotube whose length is 100 µm, the resistance R in the axis of the nanotube is between 0.1 and 100 ohms; for a mat of nanotubes having sides of 1 cm, the cross resistance is between 10 and 500 ohms.

Whether the composite material is used in the present invention as membrane or electrode, it is to be noted that the use of an insulating filling matrix is advantageous. The use of an insulating filling matrix allows an increase in the field effect of the nanotubes, and of the mat of nanotubes in particular, by reducing the screening effect of the nanotubes and of the mat in particular. It can be estimated that at least a factor of 10 is gained thereby (when using such an invention compared with a mat alone).

Similarly, whether the composite material is used as membrane or electrode, it may be in different forms such as a planar, nanostructured or spiral-wound form.

The device of the invention, in addition to the composite material such as previously defined, further comprises means allowing this material to be subjected to an electric field thereby obtaining its polarisation and hence the generating of the field effect.

Any means allowing a material to be subjected to an electric field can be used in the present invention. Advantageously, the means used in the present invention are chosen from among electrical contacts, one or more electrodes and a voltage source.

More particularly the means used in the present invention are at least one electrode, and at least one voltage source electrically connected to the composite material such as previously defined and to said at least one electrode. Said at least one electrode in the present invention is also called a <<counter-electrode>>. It is to be noted that the composite material according to the present invention and the counter-electrode must be electrically insulated.

This electrode may be in any material commonly used for an electrode. As non-limiting examples, mention can be made of an electrode comprising one or more layers in a metal material chosen from among copper, silver, platinum, cobalt, gold, titanium, palladium, chromium, aluminium and alloys thereof. Advantageously, the electrode used can be coated with an insulating layer, in particular in oxide. As a variant, this electrode can be in the form of a wire in an aforementioned material.

In one particular embodiment, this electrode may be in a composite material such as previously defined.

Also, the device of the present invention may comprise at least two electrodes in addition to the composite material.

Any electric voltage generator known to those skilled in the art can be used in the present invention, as voltage source. The voltage generated by the voltage source used in the device of the invention may be pulsed alternating or direct. Therefore the electric field to which the composite material of the device of the invention is subjected may be continuous or variable.

Advantageously, to apply the electrolysis strategy (oxidation of cells and bubbling), the voltage is direct.

To implement the electroporation strategy, this voltage is pulsed. The electric voltage generator in particular allows the supplying of pulsed voltage power with a voltage equal to or lower than 1000 V, a pulse duration of between 0.1 μs and 100 ms and, particularly between 0.5 μs and 10 ms, and a pulse frequency equal to or lower than 100 kHz. All or part of the device according to the invention can be arranged in a liquid medium. Advantageously the composite material and the counter-electrode are arranged in a liquid medium which, as examples, may be a solution, emulsion or micro-emulsion. The different types of liquid medium which can be envisaged are explained below.

It is to be noted that the values of all the voltages are given in the present invention in the form of absolute values and are to be understood as possibly being positive or negative. Therefore, when a pulsed voltage is applied, the voltage applied to each pulse may be positive or negative and the voltages applied for two consecutive pulses may be of the same or of opposite sign. It may also be a pulse of variable alternating frequency (wobulation).

In a liquid medium, in particular in the presence of water, the use of the tip enhancement effect may lead to enhancing the separation mechanism of the water molecules into molecules of di-hydrogen and di-oxygen, better known under the name <<water electrolysis>>. Two of the effects of water electrolysis under the action of an electric field are:
- the possible oxidising of molecules and hence their degradation;
- the possible creating of bubbles in the vicinity of the surface of the composite material, such as a membrane, an electrode or coating, which could allow the detaching of the biofilm adhering thereto.

Advantage can also be taken of the use of these two phenomena in the present invention in addition to the electroporation techniques since they require the use of a direct, non-variable voltage. The phenomenon of water electrolysis can easily be evidenced. By placing the composite material invention in water in the presence of a counter-electrode of wire type and by applying a voltage of 5 V in particular, the onset of bubbling on the surface of the composite material is an indication of this electrolysis.

As a variant, all or part of the device of the invention can be arranged on a support such as a biochip, a well of a multi-well plate used in biology or biotechnologies, a receptacle or container used in the agrifood industry for preservation or treatment of foodstuffs such as milk or fruit juices. Advantageously, the composite material and the counter-electrode are arranged on such support.

The present invention concerns the use of a device according to the invention to defoul the surface and/or pores of the composite material such as previously defined or to modify a composite material such as previously defined.

By <<defouling>> in the present invention is meant to prevent, reduce and/or eliminate fouling.

Therefore the present invention concerns a method for preventing, reducing and/or eliminating the fouling of a composite material, and more particularly fouling on the surface, at and in the pores (i.e. inside the nanotubes) of the composite material such as previously defined, comprising a step consisting in subjecting said composite material to an electric field. Said method uses the device of the invention such as previously defined.

Said method can be applied whether the composite material is in the form of a membrane, electrode or hydrophobic coating. This method advantageously concerns the fouling of membranes particularly used for filtration.

In the present invention by <<method for preventing fouling>> is meant a preventive method applied to the composite material and in particular to a nanotube-based porous membrane according to the invention which prevents any onset of mineral or organic germination. In fact the material or the membrane resists fouling. In this case, the electric field is generated before any use of the material or membrane to protect them against fouling on the surface, at the pores and in the pores (i.e. inside the nanotubes).

The values in the examples and the variants given below concern a composite material comprising carbon nanotubes having:
- a variable CNT density in particular of between $10^4$ and $10^{13}$ nanotubes/cm² of material;
- CNTs having outer diameters of between 2 and 500 nm, advantageously between 5 and 100 nm and more particularly between 5 and 80 nm;
- CNTs having inner diameters of between 0.5 and 100 nm, advantageously between 1 and 30 nm and more particularly between 2 and 20 nm;
- the length of the CNTs corresponds to the thickness of the material and lies between 1 μm and 1 mm, in particular between 2 et 800 μm and more particularly between 3 and 100 μm.

In a $1^{st}$ variant and as an example, the preventive method of the invention can be implemented using a constant electric field to which a composite material of the invention having carbon nanotubes is subjected by applying a constant voltage of between 0.1 and 100 V, particularly between 1 and 50 V, for a time of 1 to 10000 s, in particular between 5 and 100 s.

In a $2^{nd}$ variant and as an example, the preventive method of the invention can be implemented using a variable electric field applied to a composite material of the invention comprising carbon nanotubes by applying a pulsed voltage of between 50 and 1000 V, in particular between 100 and 500 V, with pulses having a duration of between 0.1 μs and 100 ms, in particular between 0.1 and 50 ms, and at a frequency between 10 Hz and 100 kHz, in particular between 50 Hz and 1000 Hz.

In the present invention by <<reducing or eliminating fouling>> is meant a curative method applied to the nanotube-based porous membrane which allows a membrane to be obtained having lesser fouling than obtained with the same membrane (i.e. with an identical composite material) used under the same conditions and for the same period of time. The method of the invention, in this case, is a method for treating a composite material or membrane of the invention in the course of use.

In a $1^{st}$ variant and as an example, the curative method can be implemented using a constant electric field applied to a composite material of the invention comprising carbon nanotubes by applying a constant voltage of between 0.1 and 100 V and in particular between 1 and 50 V, for a time of between 1 to 10000 s, and in particular between 10 and 8000 s.

In a $2^{nd}$ variant and as an example, the curative method can be implemented using a constant electric field to which a composite material of the invention comprising carbon nanotubes is subjected, by applying a pulsed voltage of between 50 and 1000 V, in particular between 200 and 900 V, with pulses having a duration of between 0.1 µs and 100 ms and in particular between 0.1 and 90 ms, and at a frequency between 10 Hz and 100 kHz, in particular between 50 and 1000 Hz.

The defouling method can be generated regularly throughout the lifetime of the composite material, either preventively or curatively.

It is to be stressed that it is possible to monitor the extent of fouling of a membrane by measuring resistance and to trigger an adapted defouling strategy. In this case, the term <<active membrane>> can be used.

The defouling method of the present invention also concerns a method allowing the cleaning of the surface of a hydrophobic coating containing carbon nanotubes such as previously defined, having superfluidity properties when a liquid e.g. water slips over its surface. For a coating subjected to an environment such that fouling may deteriorate its superfluidity qualities, e.g. a marine anti-fouling coating constantly in contact with seawater, the two cleaning strategies i.e. de-fouling strategies presented above can also be applied.

In addition, nanotubes are also known for their ability to reinforce a composite material, in particular a piezoelectric composite material. The use of nanotubes, when the matrix is a piezoelectric composite material, allows an improvement in the piezoelectric performance of the basic material [21] and hence allows the implementing of conventional declogging/defouling techniques via piezoelectric vibration effect.

The present invention also concerns a method for modifying a composite material such as previously defined, comprising a step consisting in subjecting said composite material to an electric field. Said method uses the device of the invention such as previously defined.

By <<to modify a composite material>> in the present invention is meant a method (1) for separating into at least two separate parts such a composite material, (2) to reduce or thin such a composite material, (3) to increase the structural quality of such a composite material and/or (4) to create a mesoporous matrix on such a composite material.

Figure 1A:
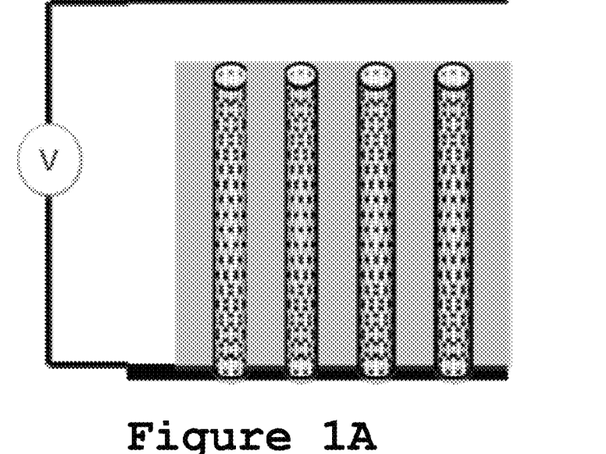

The field effect previously described can be used to separate into at least two separate parts a composite material such as previously defined i.e. to split this composite material through its thickness. FIG. 1A illustrates such splitting. For such use and as an example, the electric field applied to a composite material comprising carbon nanotubes is obtained by applying a pulsed voltage higher than 1 kV, in particular between 2 and 100 kV, with pulses having a duration of between 0.1 µs and 100 ms, in particular between 0.1 and 90 ms and at a frequency between 10 Hz and 100 kHz, in particular between 50 and 1000 Hz.

Figure 1B:
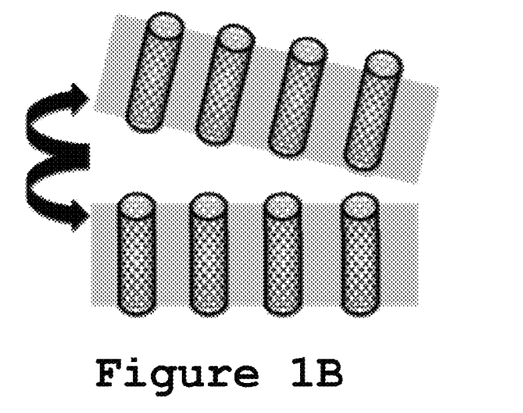

The field effect previously described can also be used to reduce the thickness of the composite material and more particularly to reduce the length of the nanotubes in the composite material, as illustrated in FIG. 1B. For such use and as an example, the electric field applied to a composite material of the invention comprising carbon nanotubes is obtained by applying a pulsed voltage higher than 1 kV, in particular between 2 and 100 kV, with pulses having a duration of between 0.1 µs and 100 ms, in particular between 0.1 and 90 ms, and at a frequency of between 10 Hz and 100 kHz, in particular between 50 and 1000 Hz.

The increase in the structural quality of the composite material and in particular of the nanotubes translates as the absence of defects in the crystalline structure of the nanotubes, continuity of the walls, the alignment and straightness of the nanotubes. It can be determined by RAMAN analyses in particular for CNTs by evaluating RBS modes and the ratio of ID/IG modes which must be as close as possible to the unit value. For example, such an increase is obtained by subjecting a composite material of the invention comprising carbon nanotubes to an electric field obtained by applying a pulsed voltage higher than 1 kV, in particular between 2 and 100 kV, with pulses having a duration of between 0.1 µs and 100 ms, in particular between 0.1 and 90 ms, and at a frequency of between 10 Hz and 100 kHz and, in particular between 50 and 1000 Hz.

Figure 1C:
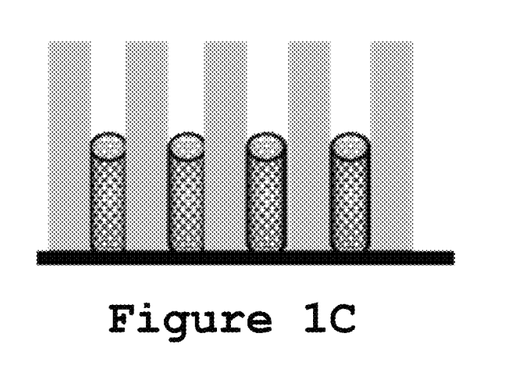
Figure 1D:
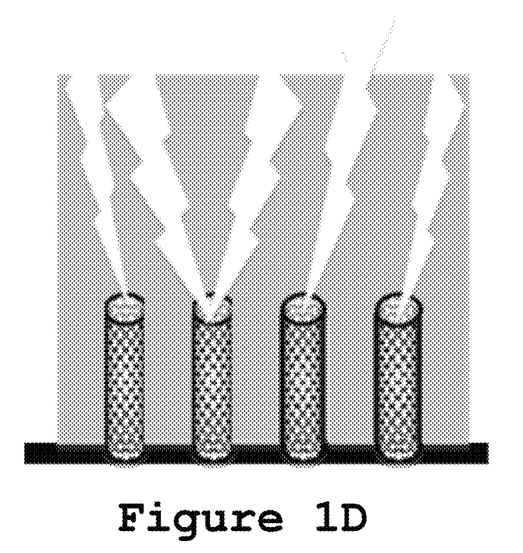

One application of the device of the invention related to the modification of a composite material such as previously defined concerns the preparation of a bi-layer membrane with a $1^{st}$ layer corresponding to said composite material and a $2^{nd}$ layer arranged on the $1^{st}$ and corresponding to a microporous membrane. This application uses a composite material such as previously defined <<embedded>> in a filling matrix, advantageously a polymer matrix, which may be the same or different from its constituent filling matrix. The application of a voltage to a membrane whose nanotubes are embedded has the effect of creating porosities directly above the nanotubes. Since the porosity thus obtained is greater than that of the nanotubes, the formed structure corresponds to the superimposition of a microporous membrane (matrix alone and in particular polymer alone) over a nanoporous membrane (mat of nanotubes that are aligned, functionalized and impregnated with filling matrix). FIG. 1C schematises this application. For such use and as an example, the electric field applied to the membrane whose carbon nanotubes are embedded in a matrix, is obtained by applying a pulsed voltage, higher than 1 kV and in particular between 2 and 100 kV, with pulses having a duration of between 0.1 µs and 100 ms, in particular between 0.1 and 90 ms, and at a frequency of between 10 Hz and 100 kHz, in particular between 50 and 1000 Hz.

Finally the present invention concerns a method for electroporating at least one cell, comprising the steps of:

α) placing said cell in the presence of a composite material such as previously defined;

β) subjecting said composite material to an electric field. Said method uses the device of the invention such as previously defined.

By <<electroporating a cell>> in the present invention is meant a method leading to damage at the plasma membrane, at the cell membrane, at the capsule and/or the cellular wall of the cell by opening pores therein and thereby permeabilizing the cell. This damage can be reversible or irreversible.

If it is reversible, the damage caused at the plasma membrane, at the cell membrane, at the capsule and/or the cellular wall only scarcely affects the cell, and is in the form of temporary cell poration and can be <<repaired>> using cell machinery.

In this case the method for electroporating at least one cell can be used for modification thereof. Therefore the method of the invention comprises an additional step to modify the electroporated cell.

This additional step comprises the contacting of the electroporated cell with an element able to cause its modification. This may entail placing the cell to be electroporated in a medium containing an element able to cause its modification together with a composite material such as previously defined prior to step (β). As a variant it may consist in placing the already electroporated cell in the presence of an element able to cause modification thereof. By <<element able to cause modification thereof>> is meant a natural or synthetic molecule, in particular a biological or biologically active molecule which is capable of transforming the cell and/or modifying its properties, characteristics and/or behaviour.

This additional step is a <<conventional>> electroporation technique. It can therefore also be used in the present invention, the benefit of which is essentially to allow the generating of fields equivalents to those of conventional electrodes but with lower voltage levels, hence easier to implement electronically, less expensive and more energy efficient.

If damage is reversible and as an example, the electric field applied at step (β), to a composite material of the invention comprising carbon nanotubes in a matrix, is obtained by applying a pulsed voltage of between 1 V and 1 kV, in particular between 10 and 100 V, with pulses having a duration of between 0.1 µs and 100 ms, in particular between 0.1 and 90 ms, and at a frequency of between 10 Hz and 100 kHz, in particular between 50 and 1000 Hz.

If the damage caused is irreversible, it may go as far as destroying the plasma membrane, the cellular membrane, the capsule and/or cellular wall and hence as far as bursting of the cell. The method for electroporating a cell according to the invention can therefore be used to eliminate or destroy said cell. On this account it finds numerous applications in the treatment and deactivation of biological waste, the treatment and preservation of foodstuffs such as mineral water, fruit juices, milk, milk beverages and others and/or for therapeutic treatment.

If damage is irreversible and as an example the electric field applied at step (β) to a composite material of the invention comprising carbon nanotubes in a matrix is obtained by applying a pulsed voltage of between 1 V and 1 kV, in particular between 10 and 100 V, with pulses having a duration of between 0.1 µs and 100 ms, in particular between 0.1 and 90 ms, and at a frequency of between 10 Hz and 100 kHz, in particular between 50 and 1000 Hz.

In the present invention, by <<cell>> is meant both a cell of prokaryote type and of eukaryote type. Among the eukaryote cells, the cell may be a yeast such as a yeast of genus *Saccharomyces* or *Candida*, an animal cell and in particular a mammalian cell, a vegetable cell or insect cell. The mammalian cells may notably be tumour cells, normal somatic line cells or stem cells. The cells of prokaryote type are bacteria which may be gram + or −. Among these bacteria, mention can be made as non-limiting, non-exhaustive examples of bacteria belonging to the phyla of spirochetes and chlamydiae, the bacteria belonging to the enterobacteriaceae families (such as *Escherichia coli*), streptococcaceae (such as *streptococcus*), micrococcaceae (such as *staphylococcus*), legionellae, mycobacteria, bacillaceae and others.

The cells used in the present invention may be in the form of a cell culture in suspension; in the form of a cell culture attached to a support such as a culture dish or multi-well dish; in the form of an ex vivo tissue; in the form of an in vivo tissue; in a liquid sample such as a foodstuff or biological waste; in a biological fluid previously extracted from a human or animal body, said sample possibly having been subjected to different prior treatment such as centrifugation, concentration, dilution . . . .

The method for electroporating at least one cell can evidently be implemented both in vivo and in vitro. Therefore, in some cases and in particular when therapy-targeted molecules are inserted in the electroporated cell(s) it can be compared with a therapeutic treatment. Consequently the present invention concerns the use of a device such as previously defined for electroporating at least one cell.

With the electroporation method of the invention, the composite material and the counter-electrode can be arranged in the liquid media previously envisaged in which the cell(s) to be electroporated are contained; in the containers containing said liquid media; on the supports on which the cell(s) to be electroporated are disposed; in the tissues containing the cell(s) to be electroporated.

In the present description, advantageous values of voltage, frequency and pulse duration are given for particular possible cases. On the basis of this teaching those skilled in the art, for a different scenario, will know how to determine the optimal values to be used taking into account influencing parameters which are:

parameters of the shape of the electrode or membrane: length of the nanotubes, density (i.e. distance between each one), diameter, number of walls of the CNTs, quality of alignment, resistance (of the nanotube and crosswise to the membrane i.e. number of connections which will reduce the field effect);

conventional electroporation parameters: type of liquid (essentially its electric conductivity, its turbidity and mobility of the species), the type and size of the cell to be electroporated and the type of cell membrane;

environmental parameters: temperature, pressure, flow etc. . . . .

The invention will be better understood on reading the following Figures and examples. These do not have the purpose of limiting the applications of the invention but are solely intended to illustrate the possibilities offered by the device and the methods of the invention.

BRIEF DESCRIPTION OF THE DRAWINGS

FIG. 1 schematises different applications of the field effect to modify a composite material comprising a mat of nanotubes impregnated in a filling matrix and subjected to a high voltage (FIG. 1A). The different schematised applications are the splitting of said composite material (FIG. 1B), the thinning of said composite material by shortening the mats of nanotubes in the matrix (FIG. 1C) and the forming of a membrane comprising said composite material on which a microporous membrane is arranged with the creation of a percolation pathway above the mats in the matrix (FIG. 1D).

FIG. 3 gives a scanning electron microscope image of a clogged/defouled membrane (FIG. 3A) and of a declogged/ defouled membrane further to the implementing of a method according to the invention (FIG. 3B).

DETAILED DESCRIPTION OF PARTICULAR EMBODIMENTS

I. Preparation of the Composite Material which can be Used in the Device of the Invention I.1. Mat of Carbon Nanotubes.

The growth of mats of nanotubes is obtained using the <<Aerosol assisted CVD>> technique on quartz (ferrocene/toluene mixture at 2.5%, Argon as carrier gas).

The mat dimension is 800 µm, the nanotubes having a mean outer diameter of 40 nm and mean inner diameter of 8 nm. The size of the mat thus obtained is 1.5 cm×1.5 cm.

The substrate is removed in a single piece using a razor blade.

I.2. Preparation of a Composite Material According to the Invention.

In a pot a few drops of stock solution of epoxy resin are deposited on the mat alone. The epoxy resin stock solution is composed of the following elements:

7.5 ml EPON (Epoxy Embedding Medium, Glycerol Glycidyl Ether);

6.5 ml MNA (Methylnadic anhydride);

0.110 ml DMP30 (2,4,6-tris(dimethylaminomethyl)phenol).

The sample is placed in an oven at 60° C. For 30 min a soft vacuum is maintained in the oven and the sample then left 16 h at this temperature. The heating is then cut off to return to normal temperature in 12 h.

The sample is thinned by mechanical polishing using abrasive discs of decreasing roughness (grain size P120, P180, P320, P600 for example to thin). Thinning is successively performed on both sides. Abrasive discs of grain size P1200, P2400 and P4000 for example are then successively used on both sides for polishing. The membrane thickness obtained is in the region of 100 µm.

The sample is cleaned with water and then ethanol to remove polishing residues.

Finally a conductive gold layer is deposited using a vacuum evaporator on only one side of the membrane. The thickness of the layer is in the order of 100 nm. Its role is solely to improve electric conduction.

Three identical membranes hereinafter designated Mem1, Mem2 and Mem3 were prepared as indicated above. Membrane Mem1 was kept intact for reference.

Membranes Mem2 and Mem3 were immersed in real saline solution (brackish water from lake Étang de Berre) for 6 months so that algae and biofilm could develop. Aerobic conditions were not controlled, only good development of the biofilm was controlled.

II. Device According to the Present Invention and Use

Figure 2:
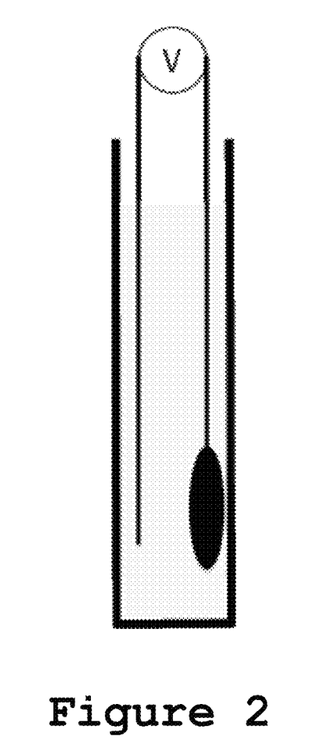
FIG. 2 schematises a device according to the present invention.

The device used is illustrated in FIG. 2.

It comprises:
membrane Mem3 with aligned CNTs and epoxy matrix prepared as described under item I after its stay in the real saline solution (Mem3);
a counter-electrode in the form of copper wire (CE);
pulsed voltage power supply (V).

More particularly, membrane Mem3 was hooked onto an electric wire by a clamp. A copper wire was provided as counter-electrode. Care was taken throughout the entire experiment that there was no contact between the two.

A current generator was used capable of producing a voltage of 100 V with pulses in the order of one microsecond. A sequence of amplitude 100 V, pulse duration 10 µs and frequency of 50 µs was applied for 10 min.

The device was placed in an electrolyte of seawater type.

III. Results

Membrane Mem2, after its stay in real saline solution described under item I, and Mem3 after the protocol described under item II were dried in an oven in a soft vacuum for 4 h for observations under microscope and comparison with membrane Mem1.

Figure 3A:
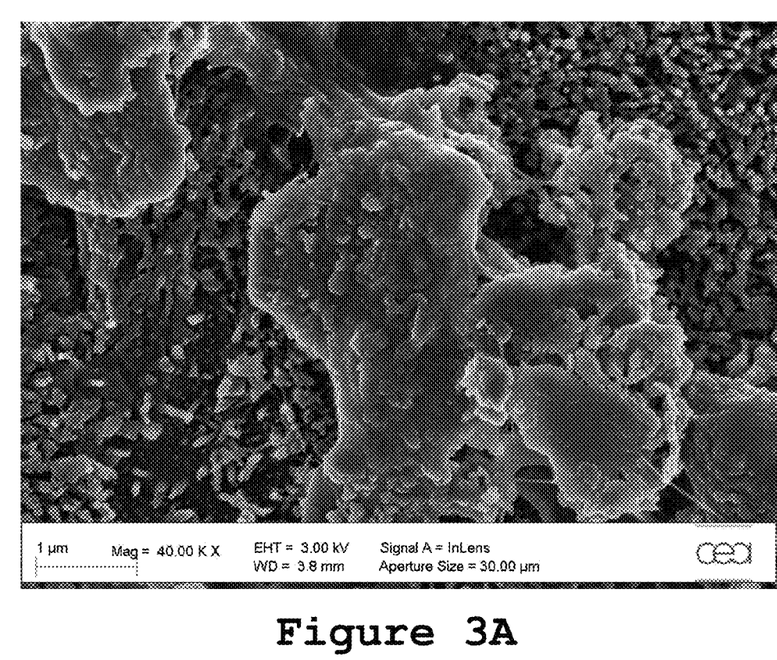
Figure 3B:
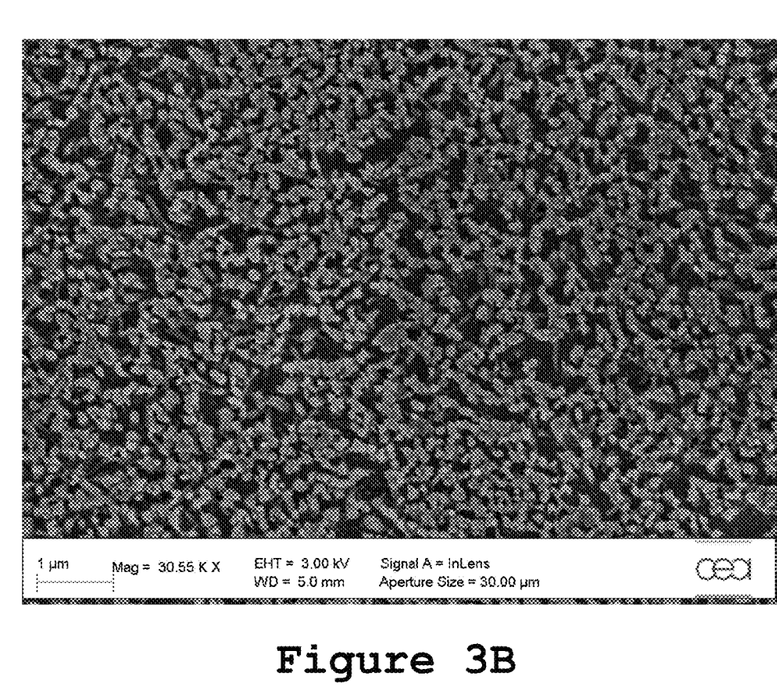

It is clearly apparent that membrane Mem3 cleaned according to a defouling method of the invention has a clean surface (FIG. 3B). This surface is close to that of the reference membrane Mem1.

On the contrary, membrane Mem2 showed fouling after its stay in real saline solution (FIG. 3A).

REFERENCES

[1] Hummer et al, 2001, <<Water conduction through the hydrophobic channel of a carbon nanotube>>, Nature, vol. 414, pages 188-190.

[2] Kang et al, 2007, <<Single-walled carbon nanotubes exhibit strong antimicrobial activity>>, Langmuir, vol. 23, pages 8670-8673.

[3] Brady-Estevez et al, 2010, <<Multi-walled nanotube filter: improving viral removal at low pressure>>, Langmuir, vol. 26, pages 14975-14982.

[4] Membrane for Water treatment, Ed. K. Peinemann and S. Pereira-Nunes, Wiley-VCH, 2010

[5] International application WO 2011/063458 filed by University of Sydney and published on 3 Jun. 2011.

[6] Cui et al, 2003, <<The use of gas bubbling to enhance membrane processes>>, J. of Membrane Sci., vol. 221, pages 1-35.

[7] Bonard et al, 2002, <<Field emission of individual carbon nanotubes in the scanning electron microscope>>, Phys Rev. Lett., vol. 89, pages 197602.

[8] Thesis by Marchand, 2009, "Synthèse in-situ et caractérisation de nanotubes de carbone individuels sous émission de champ>>, Université de Lyon, paragraphs 2.3.1 and 2.3.2, pages 62 to 64.

[9] Yantzi and Yeow, 2005, <<Carbon nanotubes enhanced pulsed electric field electroporation for medical applications>>, Mechatronics and automation, 2005 IEEE International Conference, vol. 4, pages 1872-1877.

[10] International application WO 2008/062378 filed by Scuola Superiore di Studi Universitari e di Perfezionamento Sant'Anna and published on 29 May 2008.

[11] Rojas-Chapana et al, 2005, <<Multi-walled carbon nanotubes for plasmid delivery into *Escherichia coli* cells>>, Lab. Chip, vol. 5, pages 536-539.

[12] International application WO 2008/028155 filed by Virginia Tech Intellectual Properties and published on 6 Mar. 2008.

[13] Patent application US 2004/0173506 filed by Doktyez et al and published on 9 Sep. 2004.

[14] International application WO 2009/141528 filed by Commissariat à l'Energie Atomique and published on 26 Nov. 2009.

[15] Pichot et al, 2004, <<Evidence of strong nanotube alignment and for iron preferential growth axis in multiwalled carbon nanotube mats>>, Applied Physics Letters, vol. 85, pages 473-475.
[16] Bahr et al, 2002, <<Covalent chemistry of single-wall carbon nanotubes>>, J. Mater. Chem., vol. 12, pages 1952-1958.
[17] International application WO 2008/078052 filed by Commissariat à I'Energie Atomique and published on 3 Jul. 2008.
[18] Mévellec et al, 2007, <<Grafting polymers on surfaces: a new powerful and versatile diazonium salt-based one-step process in aqueous media>>, Chem. Mater., vol. 19, pages 6323-6330.
[19] Tessier et al, 2008, <<Grafting organic polymer films on surfaces of carbon nano-tubes by Surface Electroinitiated Emulsion Polymerization>>, Physica Status Solidi A, vol. 205, pages 1412-1418.
[20] Fan et al, 2007, <<Synthesis of polymer grafted carbon nanotubes by nitroxide mediated radical polymerization in the presence of spin*-labeled carbon nanotubes>>, Macromolecular Nanotechnology, vol. 43, pages 26-34.
[21] Tian and Wang, 2008, <<Fabrication and performances of epoxy/multi-walled carbon nanotubes/piezoelectric ceramic composites as rigid piezo-damping material>>, J. Mater. Sci., vol. 43, pages 4979-4987.

The invention claimed is:

1. A method for preventing, reducing and/or eliminating the fouling of a composite material comprising (1) a plurality of conductive or semiconductive nanotubes which are aligned parallel to one another, and (2) a matrix arranged between said conductive or semiconductive nanotubes, said composite material in the form of an isoporous membrane with nanopores which correspond to the pores of said conductive or semiconductive nanotubes and optionally to the pores of said matrix arranged between said conductive or semiconductive nanotubes, said method comprising applying an electric field to said composite material, wherein the fouling is prevented, reduced and/or eliminated at the surface, at and in the pores of the composite material, wherein the electric field applied to said composite material is either a constant electric field obtained by applying a constant voltage of between 0.1 and 100 V for a time of 1 to 10000 s or a variable electric field obtained by applying a pulsed voltage of between 50 and 1000 V with pulses having a duration of between 0.1 µs and 100 ms and at a frequency between 10 Hz and 100 kHz.

2. The method according to claim 1, wherein all or part of the conductive or semiconductive nanotubes are inorganic nanotubes selected from the group consisting of nanotubes of zinc oxide (ZnO), nanotubes of gallium nitride (GaN), nanotubes of boron nitride (BN), nanotubes of tungsten bisulfide ($WS_2$), nanotubes of molybdenum bisulfide ($MoS_2$), nanotubes of tungsten diselenide ($WSe_2$), nanotubes of titanium dioxide ($TiO_2$), nanotubes of molybdenum trioxide ($MoO_3$), and a mixture thereof.

3. The method according to claim 1, wherein all or part of the conductive or semiconductive nanotubes are organic nanotubes.

4. The method according to claim 1 further comprising at least one organic polymer covalently grafted onto the conductive or semiconductive nanotubes, and wherein the at least one organic polymer is only covalently grafted onto the outer lateral part of the nanotubes.

5. The method according to claim 1, wherein said matrix is selected from the group consisting of a ceramic matrix, polymer matrix, metal matrix, a matrix derived from biomass, a matrix derived from cellulose derivatives and mixtures thereof.

* * * * *